United States Patent
Cohen et al.

(10) Patent No.: US 8,796,452 B2
(45) Date of Patent: Aug. 5, 2014

(54) PREPARATION OF LAMIVUDINE FORM I

(75) Inventors: Benjamin Cohen, Cranford, NJ (US); Christopher Wahl, Philadelphia, PA (US); Itzia Z. Arroyo, Union, NJ (US); Aaron S. Cote, West Windsor, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/577,584

(22) PCT Filed: Feb. 10, 2011

(86) PCT No.: PCT/US2011/024270
§ 371 (c)(1),
(2), (4) Date: Aug. 8, 2012

(87) PCT Pub. No.: WO2011/100381
PCT Pub. Date: Aug. 18, 2011

(65) Prior Publication Data
US 2012/0316339 A1 Dec. 13, 2012

Related U.S. Application Data

(60) Provisional application No. 61/303,858, filed on Feb. 12, 2010.

(51) Int. Cl.
*C07D 411/04* (2006.01)
(52) U.S. Cl.
USPC .......................................................... 544/317
(58) Field of Classification Search
USPC .......................................................... 544/317
See application file for complete search history.

(56) References Cited

U.S. PATENT DOCUMENTS 5,905,082 A * 5/1999 Roberts et al. ................ 514/274
2009/0281053 A1 11/2009 Singh et al.

FOREIGN PATENT DOCUMENTS

| CA | 2688142 A1 | 11/2008 | |
|---|---|---|---|
| EP | 0517145 B1 | 9/1992 | |
| WO | 03-027106 A1 | 4/2003 | |
| WO | 2007-119248 A1 | 10/2007 | |
| WO | 2008-114279 A2 | 9/2008 | |
| WO | 2009-037538 A2 | 3/2009 | |
| WO | WO 2009037538 A2 * | 3/2009 | ........... C07D 411/04 |
| WO | 2009-069013 A1 | 6/2009 | |
| WO | 2009-127996 A1 | 10/2009 | |
| WO | 91-17159 A1 | 11/2011 | |

OTHER PUBLICATIONS

Jozwiakowski, et al., "Solubility Behavior of Lamivudine Crystal Forms in Recrystallization Solvents", J. Pharm. Sci., 1996, pp. 193-199, vol. 85, No. 2.
Harris, et al., "Polymorphism in a Novel Anti-Viral Agent: Lamivudine", J. Chem. Soc., Perkin Trans, 1997, pp. 2653-2659, vol. 2.
Variankaval, et al., "Water Activity-Mediated Control of Crystalline Phases of an Active Pharmaceutical Ingredient", Organic Process R&D, 2007, pp. 229-236, vol. 11.
Renon, et al., "Local Compositions in Thermodynamic Excess Functions for Liquid Mixtures", AIChE Journal, 1968, pp. 135-144, vol. 14.

* cited by examiner

*Primary Examiner* — Kristin Vajda
(74) *Attorney, Agent, or Firm* — Jeffrey P. Bergman; Sheldon O. Heber (57) ABSTRACT

A thermodynamically controlled process for preparing Form I polymorph of lamivudine is described, wherein the process involves crystallizing Form I at a temperature of from about 0° C. to about 50° C. from a mixture which comprises (a) lamivudine or an acid salt thereof or both, (b) a solvent system comprising water and at least one organic solvent, and optionally (c) Form I seed; wherein, when a lamivudine acid salt is employed in the mixture, the crystallizing step is conducted in the presence of a base; and wherein the water activity of the solvent system is maintained in a range in which Form I is thermodynamically the most stable form of lamivudine.

25 Claims, 8 Drawing Sheets

PREPARATION OF LAMIVUDINE FORM I

CROSS-REFERENCE TO RELATED APPLICATIONS

This application is the national stage application under 35 U.S.C. 371 of International Patent Application No. PCT/US2011/024270, filed Feb. 10, 2011, which claims priority to U.S. Provisional Application No. 61/303,858, filed Feb. 12, 2010. Each of the aforementioned PCT and priority applications is incorporated by reference in its entirety.

FIELD OF THE INVENTION

The invention is directed to the preparation of the polymorph of lamivudine known as Form I via processes which involve the crystallizing lamivudine under conditions in which Form 1 is thermodynamically the most stable form of lamivudine.

BACKGROUND OF THE INVENTION

Lamivudine (alternatively referred to herein as LMV, and often typically referred to in the art as 3TC) is an antiviral drug that is presently marketed as EPIVIR (GlaxoSmithKline) for the treatment of HIV, HBV and HTLV. Chemically lamivudine is (−)-cis-4-amino-1-(2-hydroxymethyl-1,3-oxathiolan-5-yl-(1H)-pyrimidin-2-one and has the following structure:

WO 91/017159 A1 discloses the preparation of lamivudine as a white powder using enzyme-mediated enantioselective catabolism of a mixture of lamivudine and its enantiomer (see Examples 4 and 5).

U.S. Pat. No. 5,905,082 discloses that LMV exhibits polymorphism and can exist as needle-shaped crystals (referred to as Form I) and bipyramidal crystals (referred to as Form II). Form I is disclosed to be less stable than Form II as certain operations such as milling are said to cause conversion of Form I to Form II. The two polymorphic forms are characterized and distinguished by their melting behavior, infrared spectra, and DSC scans. The reference discloses that Form I can be obtained by crystallization from aqueous solution or by azeotropic distillation with 1-propanol, and that Form II can be obtained by recrystallization of LMV from non-aqueous media, in particular a $C_{2-6}$ alcohol, industrial methylated spirit (IMS; denatured ethanol) or 1-propanol. The reference also reports that Form II can be obtained by heating Form I above its melting point and allowing the melt to cool or, alternatively, by grinding or milling Form I. Example 1 in US '082 discloses the preparation of Form I by heating a suspension of LMV (referred to as "Intermediate 5" in the example) in water to 45° C. to obtain a solution, and then cooling the solution to 30° C. to provide an unstirrable crystalline mass which was broken up into a suspension that was stirred at ca. 10° C. for 1 hour. The product was then filtered, washed twice with IMS, and dried in vacuo at 45° C. for 24 hours to provide fine needle crystals (Form I). Example 2 discloses the preparation of Form II by refluxing a suspension of Form I in IMS to provide a solution, filtering the hot solution, distilling the filtrate, seeding the distilled filtrate, and cooling from 80° C. to 25° C. over 1 hour. The product isolated therefrom was aggregates of bipyramids (Form II). Example 3 discloses the formation of 100% Form II from Form I by heating a suspension of Form I from Example 1 in IMS with stirring at 50° C. for a total of about 25 hours, then cooling to 20° C. and stirring the suspension for 1 hour, and then isolating Form II therefrom.

Jozwiakowski et al., *J. Pharm. Sci.* 1996, 85 (2), pp. 193-199 discloses the preparation of Form I by dissolving LMV in hot water, adding an equal volume of MeOH, and cooling in a refrigerator. Form I and Form II were characterized by SEM, polarized light microscopy, TGA, DSC, and XRPD. The reference describes Form I as an 0.2 hydrate and Form II as an anhydrate. The reference also describes the solubility behavior of Forms I and II in various recrystallization solvents (i.e., water, MeOH, EtOH, n-PrOH, 2-PrOH, n-BuOH, sec-BuOH, EtOAc, acetone, and acetonitrile) at 5° C., 15° C., 25° C., 35° C. and 45° C. The solubility behavior of the crystalline forms in EtOH-water mixtures at 25° C. was also investigated, and it was disclosed that >18-20% water must be present in EtOH to convert the excess solid to Form I at equilibrium.

Harris et al., *J. Chem. Soc., Perkin Trans.* 2 1997, 2653-2659 provides a further study characterizing and comparing Forms I and II. It is disclosed that Form I was crystallized as needles from solutions in water, methanol, or aqueous alcohols and that Form II was obtained as bipyramids on slow recrystallization from dry EtOH, n-PrOH, or mixtures of EtOH with less polar organic solvents. The two forms were characterized by DSC, $^{13}C$ and $^1H$ NMR, IR and XRPD. Among its findings was that Form II has a highly symmetrical lattice and Form I has an asymmetric unit containing 5 non-equivalent molecules and one water molecule for every 5 of LMV (i.e., 0.2 mol hydrate).

WO 03/027106 A1 discloses a process for the preparation of Form II in which LMV salicylate is suspended in a solvent selected from aliphatic ketones, esters, and $C_{1-8}$ straight or branched-chain ethers, refluxing the suspension at the reflux temperature of the solvent, adding organic base at the reflux temperature, and then cooling the mixture and filtering to obtain Form II. The process is illustrated in Example 1 (solvent=EtOAc, base=TEA) and Example 2 (solvent=acetonitrile, base=TEA).

WO 2007/119248 A1 discloses a crystalline hemihydrate of lamivudine which is referred to therein as Form III. The reference provides a method for preparing Form III by dissolving LMV in water at 45° C., cooling the resulting solution to 30° C., optionally seeding with Form III crystals, further cooling to 10° C. at a range of 0.5° C./minute to 3.5° C./minute, and then isolating the crystals by filtration optionally washing with alcohol and drying at 45-55° C. Examples 14 and 15 respectively describe the preparation of Form I and Form. II using substantially the same procedures as set forth in Examples 1 and 2 respectively in U.S. Pat. No. 5,905,082.

WO 2008/114279 A2 discloses the preparation and characterization of an amorphous form of LMV, a crystalline solvate of LMV and dimethylacetamide (referred to therein as Form III), a crystalline solvate of LMV and 1-methyl-2-pyrrolidinone (referred to therein as Form IV), and a crystalline anhydrous polymorph of LMV referred to therein as Form V. The Form III reported in this reference (a DMAC solvate) and the Form III reported in WO 2007/119248 discussed above (crystalline hemihydrate) are not the same form of LMV. The term "Form III" as used herein refers to the crystalline hemihydrate.

WO 2008/114279 discloses that the amorphous form of LMV can be prepared by heating Form V to form a melt and then cooling the melt and that Form I can be obtained from the amorphous form. It is disclosed that Form I can be prepared by storing the amorphous LMV form at a relative humidity of >90% for several days (see Example 28), and can also be prepared by heating the amorphous LMV form at about 40° C. for several days (see Example 29). The reference also includes several examples disclosing the preparation of Form I by processes that involve cooling a hot solution of LMV in organic solvent(s) to ambient temperature. The reference also discloses examples of the preparation of Form I by the fast evaporation of a solution of LMV in organic solvent on a watch glass, and by stirring a suspension of the amorphous LMV in organic solvent at ambient temperature overnight.

WO 2009/037538 A2 discloses three processes for the preparation of Form I. The first process involves dissolving LMV in an aqueous alcohol (e.g., 15-20% aqueous EtOH at 35-60° C., preferably 45-55° C.); filtering the solution through celite; removing the alcohol under reduced pressure below 42° C.; precipitating the product from the residue by addition of EtOAc or methyl isobutyl ketone; and filtering and drying the wet material (e.g., at 40-50° C.) under reduced pressure until the water content is ≤1.8% w/w. The first process is exemplified by Examples 1 (aqueous EtOH; EtOAc), 3 (aqueous MeOH; EtOAc) and 4 (aqueous EtOH; methyl isobutyl ketone). The second process comprises treating LMV salicylate monohydrate with an organic base in an organic solvent and isolating Form I. The second process is exemplified in Examples 2 (temperature=25-30° C.; base=TEA; solvent=EtOAc) and 5 (temperature=25-30° C.; base=TEA; solvent=methyl isobutyl ketone). The third process involves slurrying LMV in a mixture of EtOAc and water and isolating Form I therefrom. The third process is illustrated in Example 6, wherein a mixture of Form I and Form II was slurried in a mixture of EtOAc (210 mL) and water (5 mL) containing TEA (0.2 g) at 20-30° C.; the slurry was stirred overnight at 20-30° C.; and the product was filtered, washed with EtOAc, and dried under reduced pressure at 40-45° C. to provide Form I.

WO 2009/069013 A1 discloses the preparation of Form I by a process which comprises dissolving LMV in water at 38-45° C. to obtain a solution, cooling the solution to a temperature of ≤30° C. in ≤10 minutes to obtain a mixture, stirring the mixture at a temperature ≤30° C. and isolating the solid therefrom, and then washing the solid with water to obtain Form I. The Form I product obtained by this process is said in the reference to be stable; i.e., the reference purports that Form I obtained by the process will not convert to Form II when subjected to milling or when stored at up to 45° C. at a relative humidity of 25% to 85%.

WO 2009/127996 A1 discloses another crystalline form of lamivudine referred to therein as Form IV. It is disclosed that Form IV can be prepared by dissolving LMV in methanol to provide a solution, cooling the resulting solution to ≤15° C. to obtain a mixture, and isolating Form IV from the mixture.

Variankaval et al., *Organic Process R&D* 2007, 11, pp. 229-236 discloses a study of the water activity-mediated control of crystalline phases of N-cyclopropyl-1-[3-[(1-oxidopyridin-3-yl)ethynyl]phenyl]-1,4-dihydro[1,8]naphthyridin-4-one-3-carboxamide. Water activities in solvent-water mixtures were calculated using the NRTL-RK model as implemented on ASPEN Properties software. The document concluded (p. 236) that the "the critical parameter in designing suitable crystallization processes in systems characterized by both anhydrous and hydrated forms is the activity of water rather than concentration in the aqueous solution." (emphasis in original)

SUMMARY OF THE INVENTION

The present invention is directed to a process for crystallizing the Form I lamivudine polymorph under conditions in which Form I is the thermodynamically most stable form. Because it is thermodynamically controlled, the process provides a robust, reliable and scalable method for crystallizing Form I which is substantially to completely free of other forms of lamivudine. Processes for producing Form I not performed under thermodynamic control rely on crystallization kinetics to produce the desired form. Since crystallization kinetics can be dependent on scale-related parameters such as mixing shear and slight variations in operating conditions, uncontrolled crystallizations can lead to variability in crystal form from lot to lot and across productions scales. The process of the invention minimizes or eliminates this potential variability. For example, traces of Form II have been observed by DSC in Form I products prepared in kinetically controlled crystallizations. Traces of Form II have not been similarly observed in Form I product prepared by the process of the invention.

More particularly, the present invention is a thermodynamically controlled process for preparing Form I of lamivudine (alternatively referred to herein as Process P) which comprises crystallizing Form I at a temperature T of from about 0° C. to about 50° C. from a mixture which comprises (a) lamivudine or an acid salt thereof or both, (b) a solvent system comprising water and at least one organic solvent, and optionally (c) Form I seed; wherein, when a lamivudine acid salt is employed in the mixture, the crystallizing step is conducted in the presence of a base; and wherein the water activity $A_w$ of the solvent system is maintained in a range in which Form I is thermodynamically the most stable form of lamivudine; and provided that when the solvent system is a binary solvent system and the temperature T is in a range of from about 20° C. to about 30° C. and the mixture from which Form I is crystallized is a slurry consisting of Form I and Form II in the binary solvent system and the process does not employ an acid salt of lamivudine (i.e., the mixture does not contain an acid salt of LMV), then the organic solvent in the binary system is other than ethyl acetate.

The mixture can include free lamivudine or an acid salt of lamivudine or a combination thereof, wherein the lamivudine and/or its acid salt can be dissolved or slurried or otherwise dispersed or suspended in the solvent system. At the start of the crystallization, the mixture can be, for example, a solution of lamivudine, a solution of an acid salt of lamivudine, a solution of two or more acid salts of lamivudine, a solution of lamivudine and one (or two or more) of its acid salts, a slurry of lamivudine, a slurry of an acid salt of lamivudine, a slurry of two or more acid salts of lamivudine, or a slurry of lamivudine and one (or 2 or more) of its acid salts. When the mixture is or contains a slurry of lamivudine, the starting slurry can contain amorphous lamivudine or a polymorph such as Form II or Form III or a mixture of two or more forms. The starting slurry can also contain Form I in an amount beyond that necessary for seeding, wherein the objective of the crystallization would be, at least in part, to produce a Form I product that is substantially free of other forms or impurities present in the starting Form I. The character of the mixture will of course change as the crystallization proceeds wherein the amount of Form I product will increase and the amount of the starting form(s) of lamivudine decrease. The crystallization is typically conducted for a time sufficient to achieve the optimal yield of Form I product. When the starting mixture is a solution, the crystallization is typically conducted for a time sufficient to maximize the yield of Form I and to minimize the amount of lamivudine remaining in solution. When the starting mixture is a slurry, the crystallization is typically conducted until no form of lamivudine other than Form I remains. Regardless of the nature of the starting mixture, when the crystallization step concludes, the ending mixture is a slurry of the Form I product substantially or completely free of other forms of lamivudine.

The solvent system employed in the crystallization comprises water and at least one organic solvent. The solvent system can be, for example, a binary solvent system consisting of water and one organic solvent, a ternary solvent system consisting of water and two organic solvents, or a quaternary or higher solvent system. Binary systems are advantageous because they are typically easier to prepare and to characterize in terms of their water activity. Furthermore, the organic solvent in a binary solvent is generally easier to separate and recover for reuse and/or environmentally appropriate disposal compared to ternary and higher systems.

An organic solvent suitable for use in Process P is an organic substance which under the crystallization conditions employed is in the liquid phase, is chemically inert, and with its water co-solvent will dissolve, suspend, and/or disperse the starting lamivudine material and any other agents present in the mixture (e.g., a base when the mixture contains an acid salt of lamivudine) so as to permit the crystallization to proceed. Representative organic solvents suitable for use in the solvent system in Process P include alcohols (e.g., alkanols), ketones (e.g., alkanones), esters of alkyl carboxylic acids (e.g., alkyl acetates), cyclic and aliphatic ethers and diethers. Suitable organic solvents are further described below.

Acid salts of lamivudine suitable for use in Process P are those salts which can react with a base to afford lamivudine in a free form. Representative acid salts suitable for use in Process P include organocarboxylates, organodicarboxylates, sulfate, bisulfate, nitrate, and hydrohalides. Suitable salts include the salts of hydroxybenzoic acids, $C_{3-10}$ alkylcarboxylic acids, $C_{3-10}$ alkyldicarboxylic acids and aromatic dicarboxylic acids. The salt can be, for example, a salt of salicylic acid, propionic acid, butyric acid, valeric acid, caproic acid, caprylic acid, malonic acid, succinic acid, glutaric acid, adipic acid, pimelic acid, phthalic acid, isophthalic acid, or terephthalic acid. Particularly suitable are the salicylate and succinate salts of lamivudine, Lamivudine salicylate is a preferred salt.

When an acid salt of lamivudine is employed, the crystallization is conducted in the presence of a base. The base can be any base which is capable of breaking the lamivudine acid salt to afford neutral lamivudine. Bases suitable for use in Process P include alkali metal hydroxides, alkali metal carbonates, and tertiary amines. The base can be, for example, a tri-$C_{1-6}$ alkyl amine (e.g., triethylamine, diisoproylethylamine, diethylisopropyl amine, or tri-n-propylamine) or pyridine. Triethylamine is a preferred base.

The base is typically employed in an amount sufficient to break all of the lamivudine acid salt. The base can suitably be employed in an amount of at least about 1 equivalent per equivalent of lamivudine acid salt, is typically employed in an amount in a range of from about 1 to about 3 equivalents (e.g., from about 1 to about 2 equivalents) per equivalent of acid salt, is more typically employed in an amount in a range of from about 1.0 to about 1.5 equivalents (e.g., from about 1.05 to about 1.2 equivalents) per equivalent of acid salt.

The crystallization is conducted in the presence or absence of Form I seed. While the crystallization process will afford Form I without seed, seeding can make the process more efficient and provide a relatively uniform product within a particular batch and more consistent product from batch to batch. Seeds are suitably employed in a amount in a range of from about 1 to about 20 wt. % based upon the weight of lamivudine employed in the crystallization, and is typically employed in an amount of from about 2 to about 6 wt. %

The water activity of the solvent system is maintained at a value or range of values in which Form I is thermodynamically the most stable form of lamivudine. The term "water activity" is defined as $f_S/f_O$ wherein $f_S$ is the fugacity of water in the solvent system of interest and $f_O$ is the fugacity of pure water at the same temperature. For systems in which the ideal gas law is valid, fugacity is equivalent to pressure. In such cases, water activity is equivalent to $p_S/p_O$, wherein $p_S$ is the vapor pressure of water in the solvent system of interest and $p_O$ is the vapor pressure of pure water at the same temperature. Water activities suitable for use in Process P and methods for their determination are described below.

A first embodiment of the present invention (alternatively referred to herein as "Embodiment PE1") is Process P as originally described (i.e., as described above), except that the proviso is changed to read as follows: and provided that when the solvent system is a binary solvent system and the temperature T is from about 20° C. to about 30° C. and an acid salt of lamivudine is not employed in the mixture, then the organic solvent is other than ethyl acetate.

A second embodiment of the present invention (Embodiment PE2) is Process P as originally described, except that the proviso is changed to read as follows: and provided that when the solvent system is a binary system and an acid salt is not employed in the mixture, then the organic solvent is other than ethyl acetate.

Additional embodiments of the present invention are either further described in or will be apparent from the ensuing description, examples, and appended claims.

DETAILED DESCRIPTION OF THE INVENTION

The present invention is directed to a thermodynamically controlled process for preparing Form I of lamivudine. Lamivudine can exist in at least three stable hydration states. Form I is a 0.2 mol hydrate; Form II is anhydrous; and Form III is a 0.5 mol hydrate. The thermodynamic stability of each of these states in an aqueous solvent system can be determined by the water activity ($A_W$) and the temperature (T) of the system. Since the hydration state of Form I lies between the hydration states of Forms II and III, the conditions under which Form I is thermodynamically stable lie between the conditions under which Forms II and III are stable.

Values of $A_W$ and T for which Form I is the most stable form in a binary solvent system were determined as follows: Physical mixtures of Forms I, II and III were added to a series of deionized water-2-butanone solvent systems having a range of water concentrations and temperatures. Each admixture was then equilibrated by aging at its temperature until the relative amounts of each crystalline form remained constant. At the completion of equilibration, each admixture contained a slurry of a single crystal form, or a slurry in which one crystal form dominates. This crystal form is the most thermodynamically stable at the admixture conditions of temperature and water concentration. Form. I was found to be thermodynamically stable in the water-2-butanone mixtures at about 0° C. when the mixtures contained from 2.5 to 5.0 wt. % water. Similarly, Form I was determined to be thermodynamically stable in water-2-butanone mixtures at about 25° C. when the mixtures contained from 3.5 to 6.0 wt. % water, and at about 50° C. when the mixtures contained from 5.0 to 8.5 wt. % water. Additional data was collected for the boundary between form I and form III; i.e., at 20° C. Form I is more stable than Form III at less than 5.7 wt % water in 2-butanone, and at 30° C. Form I is more stable than Form III at less than 6.6 wt % water. The data are shown in a phase map of temperature versus wt. % water in FIG. 1.

The water activities of the water-2-butanone mixtures were calculated using the non-random two-liquid-Redlich-Kwong (NRTL-RK) model. This model couples the non-random two-liquid equation which calculates excess Gibbs energies of liquid mixtures, and the Redlich-Kwong equation of state, which relates the state properties of pressure, temperature, and volume in the gas phase. In the NRTL portion of the model, an equation is provided for calculating partial molar excess Gibbs energy. Partial molar excess Gibbs energy is a representation of the non-ideality of a system, and is related to the activity coefficient of a liquid in a mixture by the equation:

$$\hat{G}_i E = RT \ln(g_i),$$

where $\hat{G}_i E$ is partial molar excess Gibbs energy of the specified component i, R is the gas constant, T is temperature, and $g_i$ is the activity coefficient for component i. Activity $A_i$ is the activity of component i, and is related to $g_i$ as follows:

$$A_i = g_i X_i,$$

where $X_i$ is the mole fraction of component i. Further description of excess Gibbs energies for liquid mixtures and the NRTL model can be found in *Perry's Chemical Engineers' Handbook*, 7$^{th}$ ed., Perry and Green, pp. 4-10 to 4-22; and in Renon et al., *AIChE Journal* 1968, 14, pp. 135-144.

The calculations were made in Aspen Properties (Version 2006, Aspen Technologies, Inc., Cambridge, Mass.). The Aspen Properties add-on to Microsoft Excel was used for the calculations. Using model inputs of temperature, pressure atmospheric pressure), the solvent type and solvent mass fraction, coupled with the "Mixture property–activity Coefficient" function of the Excel add-on, the water activities were obtained. For the reverse calculations (i.e., converting a desired water activity to a specific water mass fraction in a particular system), the mass fractions were iterated until the target water activity was obtained.

Figure 1:
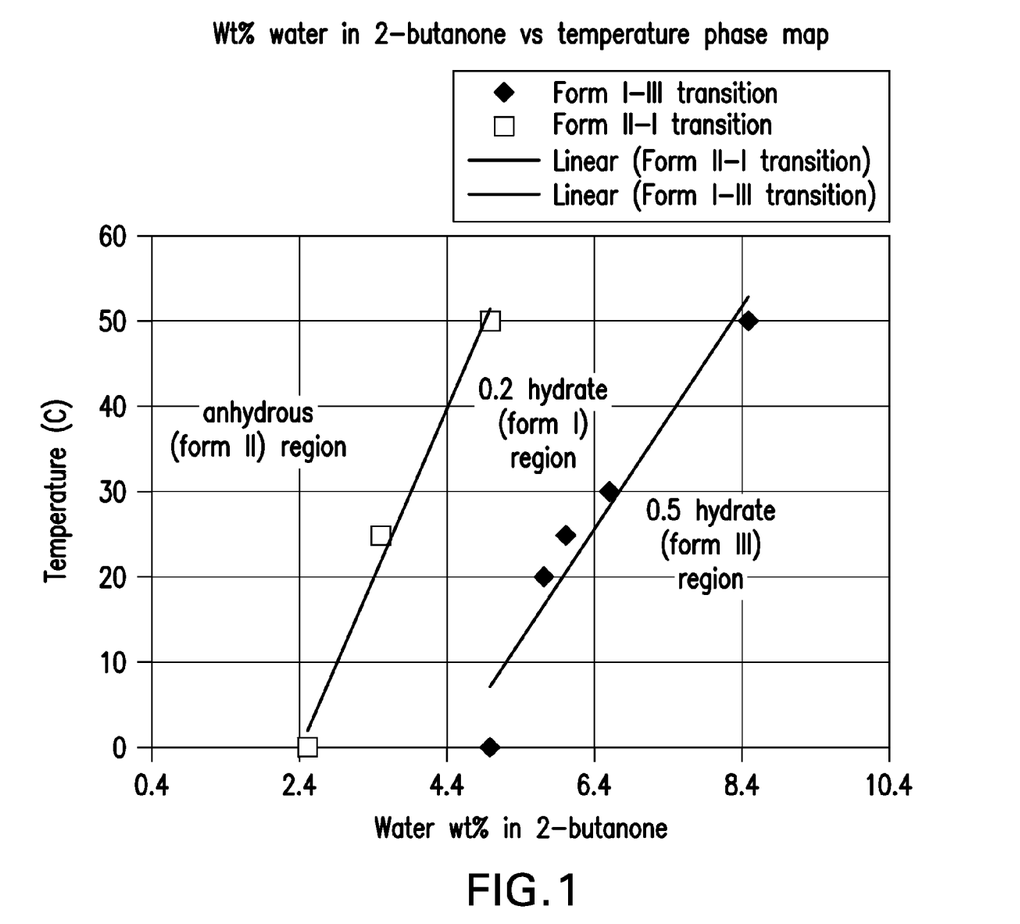
FIG. 1 is a phase map showing the thermodynamically stable forms of lamivudine in binary mixtures of water and 2-butanone in terms of weight percent water and temperature.
Figure 2:
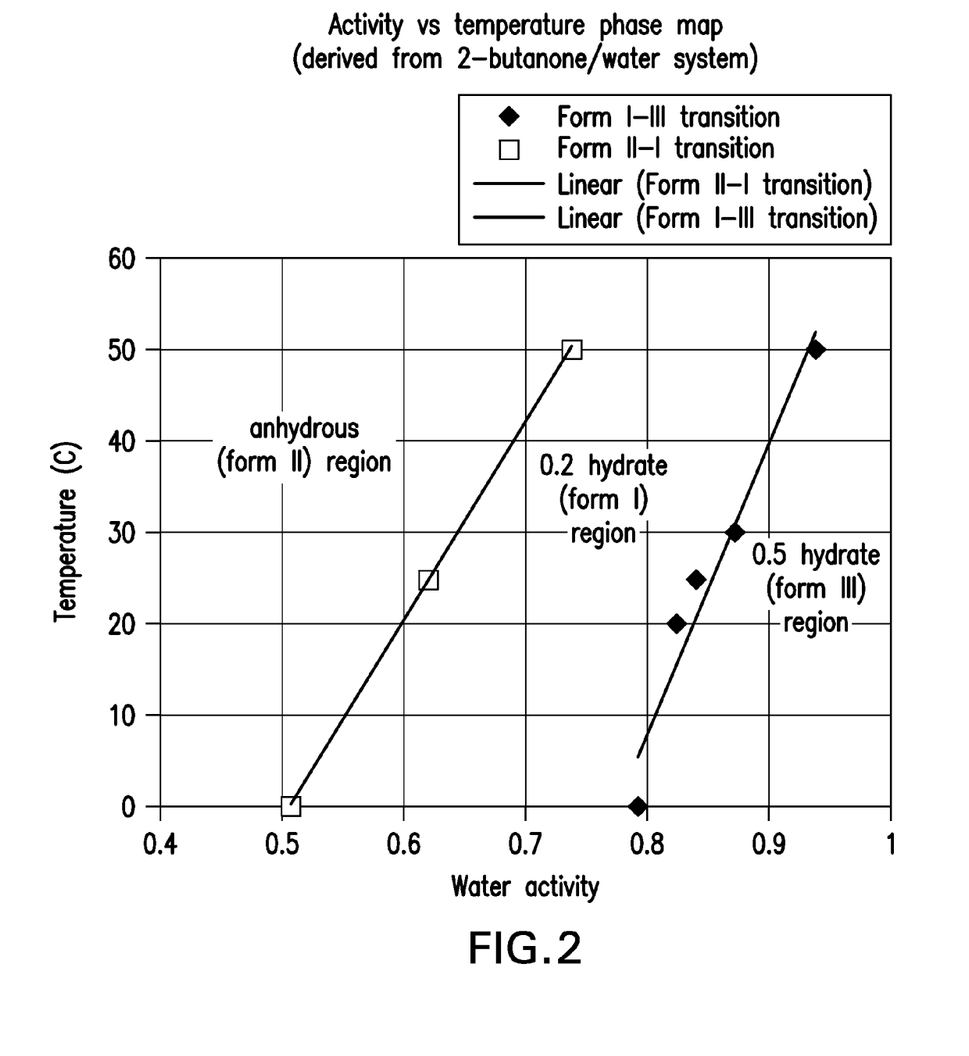
FIG. 2 is a phase map showing the thermodynamically stable forms of lamivudine in terms of water activity and temperature for binary mixtures of water and an organic solvent.

The equilibration data described above for 2-butanone-water systems and depicted in FIG. 1 was employed to calculate the corresponding water activities, from which the phase map shown in FIG. 2 was constructed in which $A_w$ and T were the two independent variables. The phase map derived from the data for the water-2-butanone system is shown in FIG. 2.

The data used to plot the transition conditions shown in FIG. 2 were subjected to linear least squares fit. The Form II to I transition was determined to have the equation:

$$A_{w1} = (0.00458 \times T) + 0.506 \quad (P).$$

The Form I to III transition was determined to have the equation:

$$A_{w2} = (0.00316 \times T) + 0.775 \quad (Q).$$

The phase map in FIG. 2 and the foregoing equations P and Q relating the water activity and temperature of the binary mixture apply in principle to binary mixtures of water with any organic solvent. Ranges of water activities marking the I-II and I-III transition conditions in binary mixtures of water at selected temperatures and with various solvents (e.g., ethyl acetate, isopropyl acetate, and ethanol) were determined using equations P and Q. The NRTL-RK model and the ASPEN Properties software were then used to determine the range of weight percents of water corresponding to each chosen range of water activity $A_w$ and temperature T. Each weight percent at a given T was determined by arbitrarily selecting a mole fraction for water and calculating its water activity, and then repeating the process in an iterative fashion until the mole fraction corresponding to the desired water activity was obtained. The mole fractions were then converted to weight percents. This procedure accordingly provided conditions under which Form I was thermodynamically the most stable form in various water-solvent binary mixtures at temperatures in a range from 0° C. to 50° C. These binary mixtures were then employed as described below to conduct thermodynamically controlled crystallizations of Form I.

Equations P and Q cannot be used for organic solvents whose physical behavior differs substantially from 2-butanone. For example, the equations cannot be applied directly to solvents which tend to form solvates with LMV. In such cases, further evaluation of the phase map for the solvent in question is necessary to determine its window of Form I thermodynamic stability.

Equations P and Q can be applied to ternary and higher mixtures of water with two or more organic solvents. However, a modified iteration procedure must be employed, because there are additional degrees of freedom (due to the presence of more than one organic solvent) which must be considered in selecting solvent mixtures.

In accordance with the foregoing description, a third embodiment of the present invention (Embodiment PE3) is Process P as originally described, wherein the solvent system is a binary system of water and one organic solvent, and the water activity of the solvent system is in a range of from about $A_{w1}$ to about $A_{w2}$ during the crystallizing step, wherein $A_{w1}$ = $(0.00458 \times T) + 0.506$ and $A_{w2} = (0.00316 \times T) + 0.775$. A first sub-embodiment of Embodiment PE3 (Sub-embodiment PE3-S1) is the process as originally described in Embodiment PE3, except that the proviso is as set forth in Embodiment PE1. A second sub-embodiment of Embodiment PE3 (Sub-embodiment PE3-S2) is the process as originally described in Embodiment PE3, except that the proviso is as set forth in Embodiment PE2. In an aspect of this embodiment and each of its sub-embodiments, the crystallization is conducted in the absence of seed. In another aspect of this embodiment and each of its sub-embodiments, the crystallization is conducted in the presence of seed.

A fourth embodiment of the present invention (Embodiment PE4) is Process P as originally described or as described in Embodiment PE3, wherein: (i) the mixture is a slurry of lamivudine acid salt and, when seeding is employed, the Form I seed in the solvent system, and (ii) the crystallizing step is conducted in the presence of base.

Aspects of Embodiment PE4 include the process as originally described in PE4 incorporating one or more of features (a1) to (a6) as follows:

(a1-a) the one or more organic solvents are selected from the group consisting of $C_{3-8}$ alkanones and $C_{1-8}$ alkyl acetates.

(a1-b) the one or more organic solvents are selected from the group consisting of 2-butanone, ethyl acetate and isopropyl acetate;

(a1-c) the organic solvent is isopropyl acetate or, if more than one organic solvent is employed, one of the solvents is isopropyl acetate;

(a2-a) the base is selected from the group consisting of alkali metal hydroxides, alkali metal carbonates, and tertiary amines;

(a2-b) the base is a tri-$C_{1-6}$ alkyl amine or pyridine;

(a2-c) the base is triethylamine, diisoproylethylamine, diethylisopropyl amine, or tri-n-propylamine;

(a2-d) the base is triethylamine;

(a3-a) the base is employed in an amount of at least about 1 equivalent per equivalent of the lamivudine acid salt;

(a3-b) the base is employed in an amount in a range of from about 1 to about 3 equivalents per equivalent of lamivudine acid salt;

(a3-b) the base is employed in an amount in a range of from about 1 to about 2 equivalents per equivalent of lamivudine acid salt;

(a3-d) the base is employed in an amount in a range of from about 1.0 to about 1.5 equivalents per equivalent of lamivudine acid salt;

(a3-e) the base is employed in an amount in a range of from about 1.05 to about 1.2 equivalents per equivalent of lamivudine acid salt;

(a4-a) the lamivudine acid salt is selected from the group consisting of organocarboxylates, organodicarboxylates, sulfate, bisulfate, nitrate, and hydrohalides;

(a4-b) the lamivudine acid salt is selected from the group consisting of hydroxybenzoic acids, $C_{3-10}$ alkylcarboxylic acids, $C_{3-10}$ alkyldicarboxylic acids and aromatic dicarboxylic acids;

(a4-c) the lamivudine acid salt is a salt of salicylic acid, propionic acid, butyric acid, valeric acid, caproic acid, caprylic acid, malonic acid, succinic acid, glutaric acid, adipic acid, pimelic acid, phthalic acid, isophthalic acid, or terephthalic acid;

(a4-d) the lamivudine acid salt is a salt of salicylic acid or succinic acid;

(a4-e) the lamivudine acid salt is lamivudine salicylate;

(a5-a) the crystallization is conducted in the presence of seed;

(a5-b) the crystallization is conducted in the absence of seed;

(a6) the solvent system is a binary system containing one organic solvent.

It is understood that each of the features (a1) to (a6) can be incorporated singly or multiply in any combination into the process of Embodiment PE4 as originally described and that the process resulting from each such incorporation is an aspect of Embodiment PE4.

A first sub-embodiment of Embodiment PE4 (Sub-embodiment PE4-S1) is the process as originally described in Embodiment PE4, wherein the base is incrementally added to the slurry during the crystallizing step. The base can be in solid form, but is typically dissolved, dispersed or suspended in the same solvent system as employed in the slurry. It is understood that each of the features (a1) to (a6) set forth above can be incorporated singly or multiply in any combination into Sub-embodiment PE4-S1 as originally described and that the process resulting from each such incorporation is an aspect of PE4-S1.

A fifth embodiment of the present invention (Embodiment PE5) is a thermodynamically controlled process for preparing Form I of lamivudine which comprises crystallizing Form I at a temperature T of from about 0° C. to about 50° C. from a mixture which comprises (a) an acid salt of lamivudine, (b) a binary solvent system comprising water and an organic solvent, and optionally (c) Form I seed; wherein the crystallizing step is conducted in the presence of a base and the water activity of the solvent system is maintained in a range of from about $A_{w1}$ to about $A_{w2}$ during the crystallizing step, wherein $A_{w1}=(0.00458 \times T)+0.506$ and $A_{w2}=(0.00316 \times T)+0.775$.

A first sub-embodiment of Embodiment PE5 (Sub-embodiment PE5-S1) is the process as originally described in Embodiment PE5, wherein the base is incrementally added to the slurry during the crystallizing step. The base can be added as a solid, or as a solution or dispersion or suspension in the same solvent system as employed in the slurry, and is typically added as a solution. The process of PE5-S1 can, for example, be conducted as follows: An acid salt of lamivudine and a solvent system containing fixed proportions of water and a selected organic solvent are charged to a crystallizer to provide a slurry of the salt in a solution of the solvent system, and the temperature of the slurry is brought to and maintained at a temperature T to afford a water activity $A_w$ for which Form I is thermodynamically the most stable form of LMV. If seeding is employed, the Form I seeds are then charged to the slurry, and then a solution of the base in a separate portion of the same solvent system is incrementally added (e.g., added drop-wise) to the slurry with agitation (e.g., stirring) of the contents of the crystallizer and with maintenance of the temperature. Upon completion of the addition of base, optionally followed by aging, the slurry now consisting of Form I is recovered using conventional means, such as separating the crystalline solid by vacuum filtration, washing the solids with the same solvent system employed in the crystallization at a temperature at or close to the temperature at which the crystallization was conducted, and then drying in a vacuum oven at a temperature and relative humidity that will not convert the Form I product to a different LMV form.

The term "aging" and variants thereof (e.g., "aged") mean allowing the crystallization to continue for a time sufficient to achieve the desired degree (usually the optimum degree) of conversion to Form I.

Each of the features (a1) to (a5) set forth above with respect to Embodiment PE4 can be incorporated singly or multiply in any combination into the process of Embodiment PE5 (or Sub-embodiment PE5-S1) as originally described and the process resulting from each such incorporation is an aspect of Embodiment PE5 (or Sub-embodiment PE5-S1). A preferred combination of base and salt is TEA and lamivudine salicylate.

Solvent systems suitable for use in Embodiment PE5 and in Sub-embodiment PE5-SE1 include, for example, water-IPAc, water-EtOAc, and water-2-butanone. The crystallization described in PE5 and PE5-S1 can, for example, be conducted using these solvent systems under the following conditions:

| Organic Solvent | Water Content (wt. %) | Temperature (° C.) | $A_W$ |
|---|---|---|---|
| IPAc | 1.1-1.7 | 25 | 0.62-0.85 |
| IPAc | 1.8-2.5 | 50 | 0.74-0.93 |
| IPAc | 1.1-1.7 | 20-30 | 0.59-0.85 |
| IPAc | 1.2-1.5 | 23-27 | 0.64-0.77 |
| EtOAc | 1.6-2.4 | 25 | 0.63-0.83 |
| EtOAc | 2.7-4.0 | 50 | 0.73-0.93 |
| EtOAc | 2.7-3.7 | 40-50 | 0.74-0.92 |
| 2-butanone | 3.5-6.0 | 25 | 0.62-0.84 |
| 2-butanone | 4.5-6.0 | 23-27 | 0.72-0.84 |

A sixth embodiment of the present invention (Embodiment PE6) is Process P as originally described or as described in Embodiment PE3, wherein the mixture is an admixture of a first component containing lamivudine acid salt dissolved in a first amount of the solvent system and a second component containing a second amount of the solvent system, base and, when seeding is employed, Form I seed.

Aspects of Embodiment PE6 include the process as originally described in PEG incorporating one or more of features (b1) to (b5) as follows:

(b1-a) the one or more organic solvents are selected from the group consisting of di-$C_{1-5}$ alkyl ethers, $C_{4-6}$ cyclic ethers, and $C_{3-5}$ dioxanes.

(b1-b) the one or more organic solvents are selected from the group consisting of ethyl ether, MTBE, n-propyl ether, isopropyl ether, THF, and 1,4-dioxane;

(b1-c) the organic solvent is THF, or, if more than one organic solvent is employed, then one of the solvents is THF;

(b2-a) the base is selected from the group consisting of alkali metal hydroxides, alkali metal carbonates, and tertiary amines;

(b2-b) the base is a tri-$C_{1-6}$ alkyl amine or pyridine;

(b2-c) the base is triethylamine, diisoproylethylamine, diethylisopropyl amine, or tri-n-propylamine;

(b2-d) the base is triethylamine;

(b3-a) the base is employed in an amount of at least about 1 equivalent per equivalent of the lamivudine acid salt;

(b3-b) the base is employed in an amount in a range of from about 1 to about 3 equivalents per equivalent of lamivudine acid salt;

(b3-b) the base is employed in an amount in a range of from about 1 to about 2 equivalents per equivalent of lamivudine acid salt;

(b3-d) the base is employed in an amount in a range of from about 1.0 to about 1.5 equivalents per equivalent of lamivudine acid salt;

(b3-e) the base is employed in an amount in a range of from about 1.05 to about 1.2 equivalents per equivalent of lamivudine acid salt;

(b4-a) the lamivudine acid salt is selected from the group consisting of organocarboxylates, organodicarboxylates, sulfate, bisulfate, nitrate, and hydrohalides;

(b4-b) the lamivudine acid salt is selected from the group consisting of hydroxybenzoic acids, $C_{3-10}$ alkylcarboxylic acids, $C_{3-10}$ alkyldicarboxylic acids and aromatic dicarboxylic acids;

(b4-c) the lamivudine acid salt is a salt of salicylic acid, propionic acid, butyric acid, valeric acid, caproic acid, caprylic acid, malonic acid, succinic acid, glutaric acid, adipic acid, pimelic acid, phthalic acid, isophthalic acid, or terephthalic acid;

(b4-d) the lamivudine acid salt is a salt of salicylic acid or succinic acid;

(b4-e) the lamivudine acid salt is lamivudine salicylate;

(b5-a) the crystallization is conducted in the presence of seed;

(b5-b) the crystallization is conducted in the absence of seed;

(b6) the solvent system is a binary system containing one organic solvent.

It is understood that each of the features (b1) to (b6) can be incorporated singly or multiply in any combination into the process of Embodiment PE6 as originally described and that the process resulting from each such incorporation is an aspect of Embodiment PE6.

A first sub-embodiment of Embodiment PE6 (Sub-embodiment PE6-S1) is the process as originally described in Embodiment PE6, wherein the admixture is formed by adding the first component to the second component, wherein the first component has a temperature higher than T prior to the addition, and the admixture is maintained at a temperature T during the crystallizing step. The first component is held at a temperature sufficient to maintain the lamivudine acid salt in solution. The first component is typically added to the second component incrementally and in such a manner so not to cause the temperature T to change to a temperature outside the range in which Form I is thermodynamically the most stable form. It is understood that each of the features (b1) to (b6) set forth above can be incorporated singly or multiply in any combination into Sub-embodiment PE6-S1 as originally described and that the process resulting from each such incorporation is an aspect of PE6-S1.

A seventh embodiment of the present invention (Embodiment PE7) is a thermodynamically controlled process for preparing Form I of lamivudine which comprises crystallizing Form I at a temperature T of from about 0° C. to about 50° C. from a mixture which comprises an admixture of a first component containing lamivudine acid salt dissolved in a first amount of a binary solvent system and a second component containing a second amount of the binary solvent system, base and, when seeding is employed, Form I seed; wherein the water activity of the solvent system is maintained in a range of from about $A_{w1}$ to about $A_{w2}$ during the crystallizing step, wherein $A_{w1}=(0.00458 \times T)+0.506$ and $A_{w2}=(0.00316 \times T)+0.775$.

A first sub-embodiment of Embodiment PE7 (Sub-embodiment PE7-S1) is the process as originally described in Embodiment PE7, wherein the admixture is formed by adding the first component to the second component, wherein the first component has a temperature higher than T prior to the addition, and the admixture is maintained at a temperature T during the crystallizing step. The first component is held at a temperature sufficient to maintain the lamivudine acid salt in solution. The first component is typically added to the second component incrementally and in such a manner so not to cause the temperature T to change to a temperature outside the range in which Form I is thermodynamically the most stable form. The process of PE7-S1 can, for example, be conducted as follows: A mixture of an acid salt of lamivudine and a binary solvent system consisting of a solution of fixed proportions of water and a selected organic solvent is heated to a temperature sufficient to dissolve the salt and provide an acid salt solution. (Note: The mixture is heated in a manner—e.g., in a sealed vessel—that will minimize or avoid the loss of the water and/or the organic solvent) A separate portion of the solvent system is added to a crystallizer and brought to and maintained at a temperature T to afford a water activity $A_w$ for which Form I is thermodynamically the most stable form of LMV. The base and, if seeding is employed, Form I seeds are then charged to the crystallizer. The separately prepared hot acid salt solution is then added incrementally (e.g., drop-wise) to the crystallizer while agitating (e.g., stirring) the crystallizer contents and maintaining the crystallizer temperature. Upon completion of the addition of hot solution, optionally followed by aging, the resulting slurry consisting of Form I is recovered using conventional means, such as separating the crystalline solid by vacuum filtration, washing the solids with the same solvent system employed in the crystallization at a temperature at or close to the temperature at which the crystallization was conducted, and then drying in a vacuum oven at a temperature and a relative humidity that will not convert the Form I product to a different LMV form.

Each of the features (b1) to (b5) set forth above with respect to Embodiment PE6 can be incorporated singly or multiply in any combination into the process of Embodiment PE7 (or Sub-embodiment PE7-S1) as originally described and the process resulting from each such incorporation is an aspect of Embodiment PE7 (or Sub-embodiment PE7-S1). A preferred combination of base and salt is TEA and lamivudine salicylate.

Solvent systems suitable for use in Embodiment PE7 and in Sub-embodiment PE7-SE1 include, for example, water-THF. The crystallization described in PE7 and PE7-S1 can, for example, be conducted using this solvent system under the following conditions:

| Organic Solvent | Water Content (wt. %) | Temperature (° C.) | $A_W$ |
| --- | --- | --- | --- |
| THF | 3-8 | 25 | 0.66-0.83 |
| THF | 1.5-6.0 | 0 | 0.52-0.80 |

An eighth embodiment of the present invention (Embodiment PE8) is Process P as originally described or as described in Embodiment PE3, wherein the mixture is an admixture of (1) a solution of lamivudine (i.e., free base LMV) dissolved in a first amount of the solvent system and (ii) a second amount of the solvent system containing, when seeding is employed, Form I seed; and wherein an acid salt of lamvivudine is not employed in the process (i.e., the mixture does not contain an acid salt of LMV).

Aspects of Embodiment PE8 include the process as originally described in PE8 incorporating one or more of features (c1) to (c3) as follows:

(c1-a) the one or more organic solvents are selected from the group consisting of $C_{3-8}$ alkanones and $C_{1-8}$ alkyl alcohols.

(c1-b) the one or more organic solvents are selected from the group consisting of 2-butanone, ethanol, and 1-propanol;

(c2-a) the crystallization is conducted in the presence of seed;

(c2-b) the crystallization is conducted in the absence of seed;

(c3) the solvent system is a binary solvent system.

It is understood that each of the features (c1) to (c3) can be incorporated singly or multiply in any combination into the process of Embodiment PE8 as originally described and that the process resulting from each such incorporation is an aspect of Embodiment PE8.

A first sub-embodiment of Embodiment PE8 (Sub-embodiment PE8-S1) is the process as originally described in Embodiment PE8, wherein the admixture is formed by adding the solution of lamivudine to the second amount of the solvent system wherein:

(i) the second amount is at temperature T, (ii) the lamivudine solution has a temperature higher than T, and (iii) the admixture is maintained at a temperature T during the crystallizing step.

In PE8-S1, the lamivudine solution is held at a temperature sufficient to maintain the lamivudine in solution. The lamivudine solution is typically added to the second amount incrementally and in such a manner so not to cause the temperature T to change to a temperature outside the range in which Form I is thermodynamically the most stable form. It is understood that each of the features (c1) to (c3) set forth above can be incorporated singly or multiply in any combination into Sub-embodiment PE8-S1 as originally described and that the process resulting from each such incorporation is an aspect of PE8-S1.

A ninth embodiment of the present invention (Embodiment PE9) is a thermodynamically controlled process for preparing Form I of lamivudine which comprises crystallizing Form I at a temperature T of from about 0° C. to about 50° C. from a mixture which is an admixture of (i) a solution of lamivudine dissolved in a first amount of a binary solvent system and (ii) a second amount of the binary solvent system optionally containing Form I seed, and wherein an acid salt of lamvivudine is not employed in the process; wherein the water activity of the solvent system is maintained in a range of from about $A_{w1}$ to about $A_{w2}$ during the crystallizing step, and wherein $A_{w1}=(0.00458\times T) 0.506$ and $A_{w2}=(0.00316\times T)+0.775$.

A first sub-embodiment of Embodiment PE9 (Sub-embodiment PE9-S1) is the process as originally described in Embodiment PE9, wherein the admixture is formed by adding the solution of lamivudine in the binary solvent sytem to the second amount of the binary solvent system wherein:

(i) the second amount is at temperature T, (ii) the lamivudine solution has a temperature higher than T, and (iii) the admixture is maintained at a temperature T during the crystallizing step.

In PE9-S1, the lamivudine solution is held at a temperature sufficient to maintain the lamivudine in solution. The lamivudine solution is typically added to the second amount incrementally and in such a manner so as not to cause the temperature T to change to a temperature outside the range in which Form I is thermodynamically the most stable form. The process of PE9-S1 can, for example, be conducted as follows: A mixture of lamivudine and a binary solvent system consisting of a solution of fixed proportions of water and a selected organic solvent are heated to a temperature sufficient to dissolve the LMV and provide a solution of LMV. (Note: The mixture is heated in a manner—e.g., in a sealed vessel—that will minimize or avoid the loss of the water and/or the organic solvent.) A separate portion of the binary solvent system is added to a crystallizer and brought to and maintained at a temperature T to afford a water activity $A_w$ for which Form I is thermodynamically the most stable form of LMV. If seeding is employed, Form I seeds are then charged to the crystallizer. The separately prepared hot LMV solution is then added incrementally (e.g., drop-wise) to the crystallizer while agitating (e.g., stirring) the crystallizer contents and maintaining the crystallizer temperature. Upon completion of the addition of the hot solution, optionally followed by aging, the resulting slurry consisting of Form I is recovered using conventional means, such as separating the crystalline solid by vacuum filtration, washing the solids with the same solvent system employed in the crystallization at a temperature at or close to the temperature at which the crystallization was conducted, and then drying in a vacuum oven at a temperature and relative humidity which will not convert the Form I product to a different LMV form.

Each of the features (c1) to (c3) set forth above with respect to Embodiment PE8 can be incorporated singly or multiply in any combination into the process of Embodiment PE9 (or Sub-embodiment PE9-S1) as originally described and the process resulting from each such incorporation is an aspect of Embodiment PE9 (or Sub-embodiment PE9-S1).

Solvent systems suitable for use in Embodiment PE9 and in Sub-embodiment PE9-SE1 include, for example, water-2-butanone, water-ethanol, and water-1-propoanol. The crystallization described in PE9 and PE9-S1 can, for example, be conducted using these solvent systems under the following conditions:

| Organic Solvent | Water Content (wt. %) | Temperature (° C.) | $A_W$ |
|---|---|---|---|
| 1-PrOH | 5.4-12.1 | 5 | 0.53-0.79 |
| EtOH | 13.9-43.0 | 5 | 0.53-0.79 |
| 2-butanone | 3.4-6.1 | 25 | 0.52-0.87 |

A tenth embodiment of the present invention (Embodiment PE10) is Process P as originally described or as described in any one of the foregoing embodiments, wherein Form I is substantially free of other forms of lamivudine. The term "substantially free" in this context means suitably at least about 90 wt. %, typically at least about 95 wt. %, preferably at least about 99 wt. %, and more preferably 100 wt. % of the lamivudine produced by and recovered from the crystallization step is Form I, as determined by a standard method of analysis. A product consisting of 100 wt. % Form I is one in which other forms of lamivudine are not detectable.

An eleventh embodiment of the present invention (Embodiment PE11) is Process P as originally described or as described in any one of the foregoing embodiments, wherein Form I is substantially pure. The term "substantially pure" in this context means suitably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of the material produced by and recovered from the crystallization consists of lamivudine. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined in a given sample, then the method providing the highest purity level governs. A compound or salt of 100% purity is one which is free of detectable impurities as determined by a standard method of analysis.

It is understood that for each of the foregoing embodiments PE3 to PE11 and sub-embodiments and aspects thereof, the proviso included in Process P as originally described applies, unless it is expressly stated therein or clear from the features recited therein that the proviso does not apply or that the proviso is implicitly satisfied. Thus, for example, the proviso applies to Embodiment PE3, but is unnecessary in PE4 because the process set forth in PE4 employs an acid salt of lamivudine. As another example, the proviso in Process P as originally described does not apply to Sub-embodiments PE3-S1 and PE3-S2, because they expressly incorporate the provisos in Embodiments PE1 and PE2 respectively. It is also understood that each of the foregoing embodiments and sub-embodiments include aspects in which the provisos set forth in Embodiments PE1 and PE2 apply in place of the original proviso, unless it is expressly stated therein or clear from the features recited therein that the proviso does not apply or that the proviso is implicitly satisfied.

Other embodiments of the present invention include the process as originally described above and any embodiments, sub-embodiments, or aspects thereof as heretofore defined, which further comprises isolating (which may be alternatively referred to as recovering) the Form I product from the crystallization medium. It is understood that the recovery of Form I is typically conducted under conditions in which essentially no conversion of Form I to one or more other forms of LMV can occur, and that the recovery can be conducted under conditions in which no conversion of Form I occurs. The recovery can, for example, be conducted under conditions in which Form I is thermodynamically the most stable form or is kinetically stable.

The term "about", when modifying the quantity (e.g., equivalents) of a substance or composition, or the value of a physical property, or the value of a parameter characterizing a process step (e.g., the temperature at which the crystallization is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In the particular case of the temperature T, the term "about" typically means the value±2° C., and in the case of water activity $A_w$, the term "about" typically means the value±0.05.

Abbreviations employed herein include the following:
DMAC N,N-dimethylacetamide;
DSC=differential scanning calorimetry;
EtOAc=ethyl acetate;
EtOH=ethanol;
HBV=hepatitis B virus;
HIV=human immunodeficiency virus;
HTLV=human T-lymphotrophic virus;
IPAc=isopropyl acetate;
MeOH=methanol;
NMR=nuclear magnetic resonance;
n-PrOH (or 1-PrOH)=n-propanol (or 1-propanol);
n-BuOH=n-butanol;
2-PrOH=2-propanol;
sec-BuOH=sec-butanol;
SEM=scanning electron microscopy;
TEA=triethylamine;
TGA=thermogravimetric analysis;
XPRD=X-ray powder diffraction The following examples serve only to illustrate the invention and its practice. The examples are not to be construed as a limitation on the scope or spirit of the invention. In these examples, "room temperature" refers to a temperature in a range of about 20-25° C. The water employed in these examples was deionized water.

Example 1

Crystallization of Lamivudine from Lamivudine Salicylate

Figure 3:
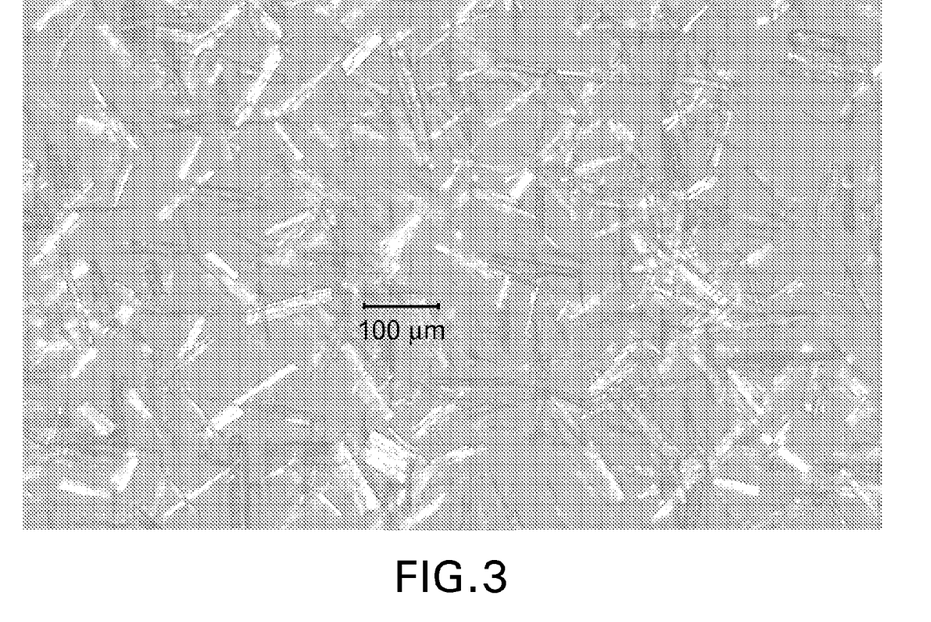
FIG. 3 is a micrograph showing the morphology of the crystalline lamivudine product of Example 1.

Lamivudine salicylate (90 g) and a solution of isopropyl acetate and water (756 mL; 1.3 wt. % water) were charged to a jacketed flask, and the temperature of the resulting slurry was brought to and maintained between 23° C. and 27° C. (corresponds to water activity between 0.68 and 0.70). Form I seeds (5.4 g) were then charged to the flask. A 2 M solution of triethylamine (128 mL of TEA in isopropyl acetate-1.3 wt. % water; 1.1 eq. with respect to the lamivudine salicylate) was then added to the flask dropwise over 10 hours while stirring the flask's contents. After the addition of TEA was complete, the resulting Form I slurry was milled with a rotor/stator wet mill (IKA) to a steady state particle size of 34 microns while maintaining the temperature between 20° C. and 30° C. The slurry was then vacuum filtered and washed with 60 mL, 140 mL and then 100 mL of the IPAc-1.3 wt. % water solution, all at room temperature. The product was then dried in a vacuum oven at 25° C. until the IPAc was fully removed. The resulting cake (53.3 g; 88% yield) was a crystalline white powder whose morphology was rod-like crystals (see FIG. 3).

Figure 4:
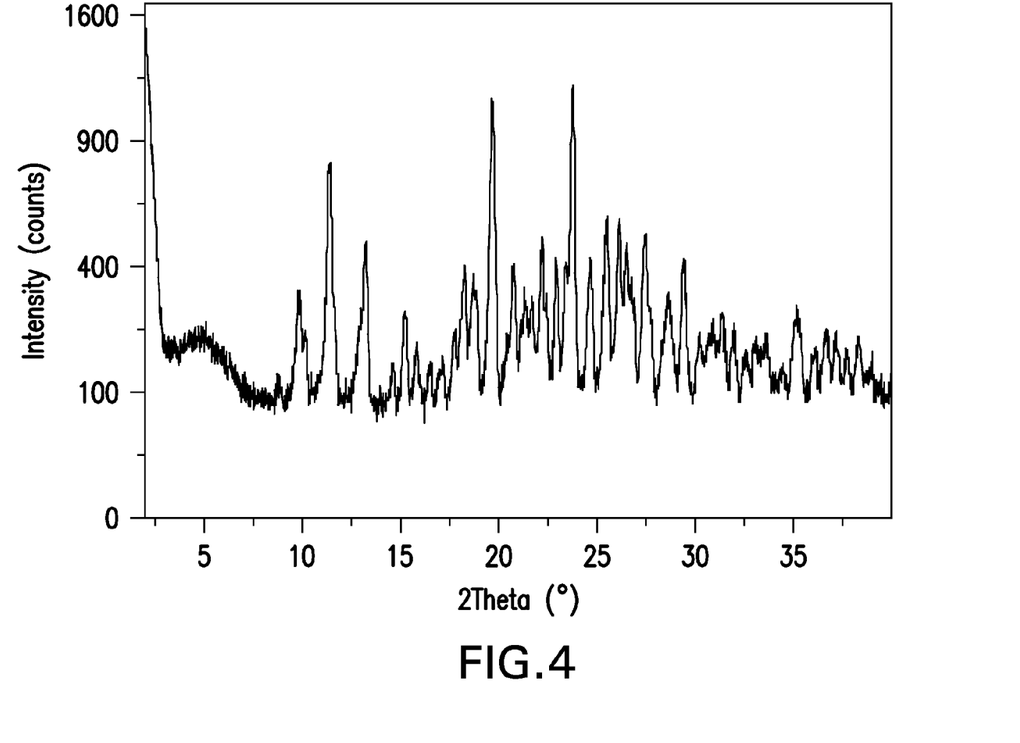
FIG. 4 is the X-ray powder diffraction pattern for the crystalline lamivudine product of Example 1.

An XRPD pattern of crystalline product was generated on a Philips Pananalytical X'Pert Pro X-ray powder diffractometer with a PW3373/10 Cu LFF DK184158 console using a continuous scan from 2.5 to 40 degrees 2Θ. Copper K-Alpha 1 ($K_{\alpha 1}$) and K-Alpha 2 ($K_{\alpha 2}$) radiation was used as the source. Approximately 30 mg of sample was placed on a silicon disk, flattened and analyzed. The experiment was conducted with the sample at room temperature and open to the atmosphere. The XRPD pattern, shown in FIG. 4, is the pattern for Form I lamivudine. 2Θ values, the corresponding d-spacings, and the relative peak intensities of the most representative diffraction peaks in the XRPD pattern include the following:

TABLE 2

XRPD of Lamivudine Form I

| Peak No. | d-spacing (Å) | 2 Theta | I/Imax (%) |
|---|---|---|---|
| 1 | 4.50985 | 19.6855 | 100 |
| 2 | 3.74456 | 20.6855 | 78.3 |
| 3 | 7.74226 | 11.4294 | 78.05 |
| 4 | 7.58282 | 11.6706 | 39.57 |
| 5 | 3.41058 | 26.1284 | 37.1 |
| 6 | 6.67281 | 13.2689 | 35.77 |
| 7 | 3.79386 | 23.449 | 32.76 |
| 8 | 4.735 | 18.7409 | 32.24 |
| 9 | 3.49423 | 25.4922 | 31.86 |
| 10 | 8.92933 | 9.9059 | 30.6 |
| 11 | 4.01047 | 22.166 | 27.29 |
| 12 | 3.96032 | 22.4503 | 26.46 |
| 13 | 4.8472 | 18.3033 | 26.39 |
| 14 | 5.58874 | 15.8579 | 26.37 |
| 15 | 4.09997 | 21.6762 | 25.37 |
| 16 | 5.80779 | 15.2561 | 23.58 |
| 17 | 4.28501 | 20.7296 | 23.39 |
| 18 | 3.25028 | 27.4416 | 22.65 |
| 19 | 3.36128 | 26.5185 | 22.42 |
| 20 | 3.87832 | 22.9314 | 22.24 |

Figure 5:
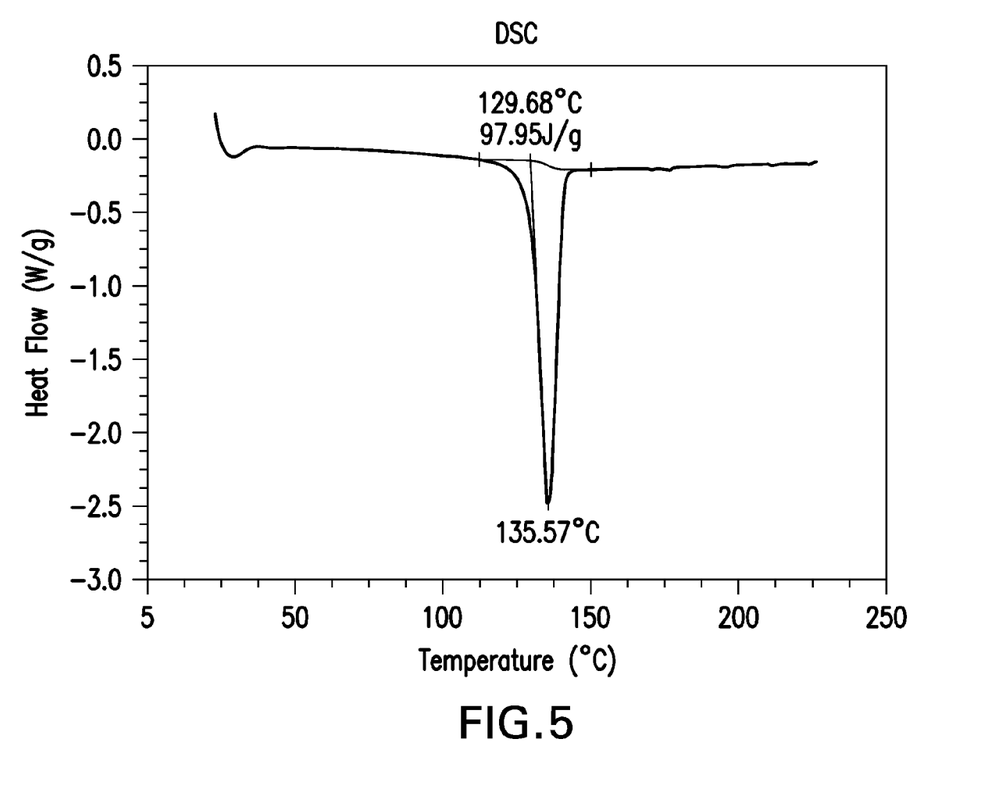
FIG. 5 is the DSC curve for the crystalline lamivudine product of Example 1.

The crystalline product (ca. 5 mg) was analyzed with a TA Instruments DSC 2910 differential scanning calorimeter (DSC) at a heating rate of 10° C./minute from 25° C. to 250° C. in an open aluminum pan in a nitrogen atmosphere. The DSC curve (see FIG. 5) exhibited an endotherm with an onset temperature of 130° C. and a peak temperature of 136° C. The enthalpy change was 98 J/g. The endotherm is associated with water loss and melting of Lamivudine Form I.

Figure 6:
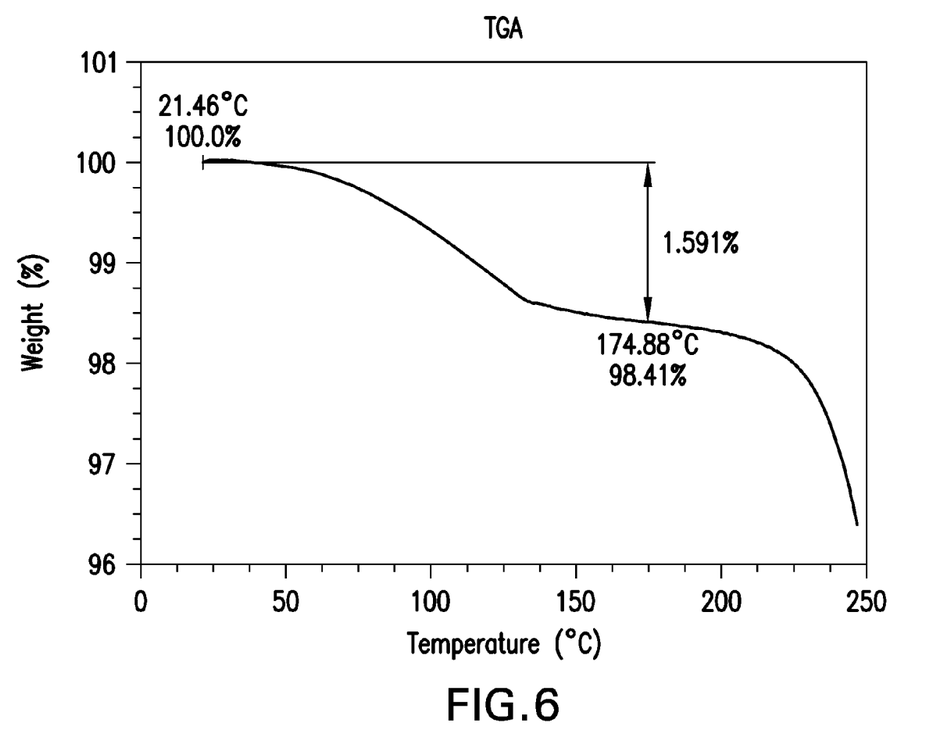
FIG. 6 is a plot of the thermogravimetric analysis for the crystalline lamivudine product of Example 1.

A thermogravimetric analysis (TGA) of the crystalline product (ca. 5 mg) was performed with a Perkin Elmer TA7 under nitrogen at a heating rate of 10° C./minute from 25° C. to 250° C. The TG curve (see FIG. 6) showed a weight loss of 1.6 wt. % up to 175° C. which is consistent with a 0.2 mol hydrate of Lamivudine (Form I).

Form. I was the only form of lamivudine detected in the crystalline product of Example 1.

Example 2

Crystallization of Lamivudine from Lamivudine Salicylate

Lamivudine was also crystallized from lamivudine salicylate in the presence of TEA under each set of conditions set forth in Table 3 following a procedure analogous to that described in Example 1, except that Examples 2A, 2B and 2C were not milled. In each case, the product provided Form I lamivudine as confirmed by XRPD, DSC and TGA. No other forms of lamivudine were detected.

TABLE 3

| Example No. | LMV Salicylate (g) | Solvent System | Crystn Temp (° C.) | Water Activity | Form I Seed (g) | TEA (eq) |
|---|---|---|---|---|---|---|
| 2A | 2 | 3.1 wt. % water-EtOAc (20 mL) | 50 | 0.80 | 0.06 | 1.1 (in 3.0 wt % water-EtOAc) |
| 2B | 2 | 1.58 wt. % water-EtOAc (20 mL) | 25 | 0.62 | 0.60 | 1.1 (in 1.58 wt % water-EtOAc) |
| 2C | 2 | 1.83 wt. % water-IPAc (20 mL) | 50 | 0.75 | 0.60 | 1.1 (in 1.83 wt % water-IPAc) |
| 2D | 4 | 6.1 wt. % water-2-butanone (25 mL) | 25 | 0.82 | 0.327 | 1.1 (in 6.1 wt % water-2-butanone) |

1. The yield was not determined for the runs in this table.

Example 3

Crystallization of Lamivudine from Lamivudine Salicylate

Figure 7:
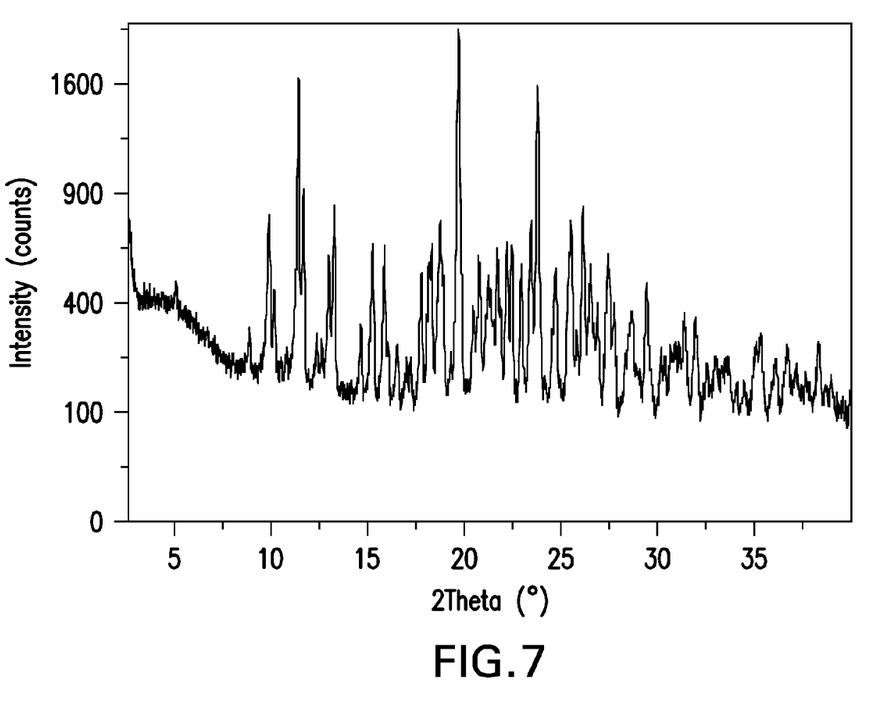
FIG. 7 is the X-ray powder diffraction pattern for the crystalline lamivudine product of Example 3.

A mixture of THF-water solution (27 mL; 2.9 wt. % water) with lamivudine salicylate (10 g) in a sealed round bottom flask was heated at 64° C. until the salicylate dissolved. A separate portion (17 mL) of the THF-2.9 wt. % water solution was charged to a jacketed flask ("crystallizer") and cooled to about 0° C. (corresponds to a water activity of 0.68), after which TEA (3.98 g, 1.1 eq.) and Form I seed (0.3 g) were charged to the crystallizer. While the crystallizer was agitated and maintained at 0° C., the hot lamivudine salicylate solution was added dropwise over 4 hours. The resulting crystalline slurry was then filtered, washed with 2×8 mL of the THF-2.9 wt. % water solution at 0° C. The product was then dried in a vacuum oven at 25° C. The XRPD (see FIG. 7), DSC and TGA of the product was obtained using the procedure described in Example 1, the results of which confirmed that the product was lamivudine Form I. No other forms of lamivudine were detected in the XRPD.

Example 4

Crystallization of Lamivudine

Figure 8:
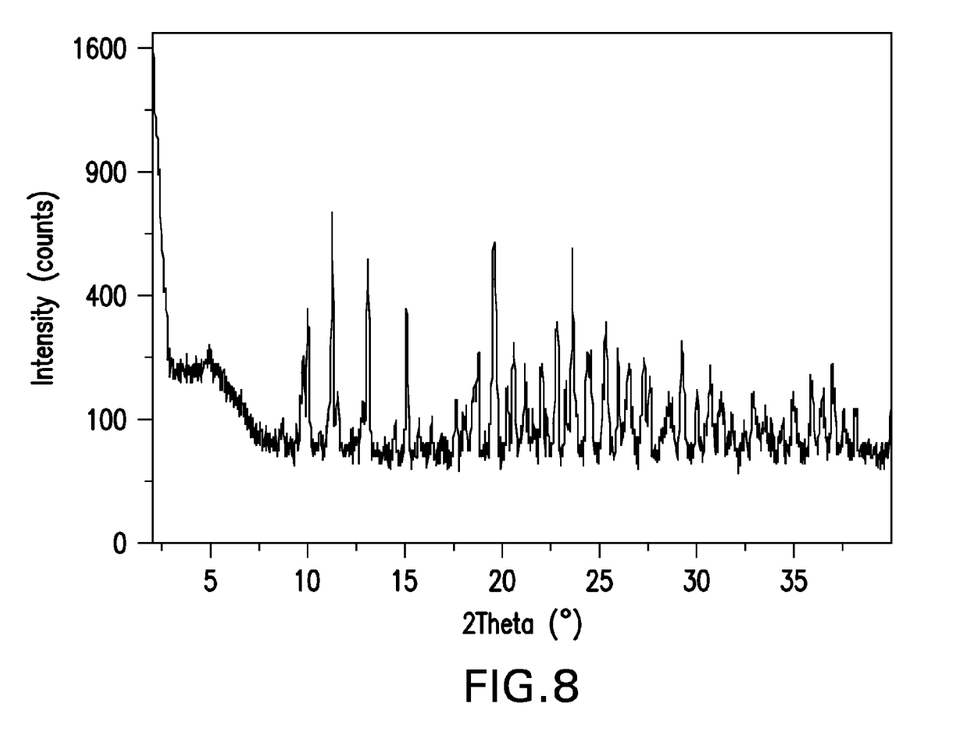
FIG. 8 is the X-ray powder diffraction pattern for the crystalline lamivudine product of Example 4.

Lamivudine Form II (5 g) was added to a solution of 1-propanol-water (72 mL; 8.7 wt. % water) in a round bottom flask, the flask was sealed, and the mixture was heated to and maintained at 60° C. at which point the lamivudine dissolved. Lamivudine Form I seed (0.35 g) and 1-propanol-water (12.5 mL; 8.7 wt. % water) were charged to a jacketed flask ("crystallizer") resulting in a slurry. The hot lamivudine solution was then charged to the crystallizer over 3 hours while the crystallizer was agitated and its temperature was maintained at 0° C. to 5° C. water activity of 0.69 to 0.70). After the addition was complete, the slurry was vacuum filtered, washed with a 1-propanol-8.7 wt. % water mixture cooled to 0-5° C., and then dried at 40° C. in a vacuum oven. The XRPD of the product (see FIG. 8) was obtained using the procedure described in Example 1, the results of which confirmed that the product was lamivudine Form I. No other forms of lamivudine were detected in the XRPD.

Example 5

Crystallization of Lamivudine

Lamivudine was also crystallized under the conditions set forth in Table 4 following a procedure analogous to that described in Example 4. The product provided Form I lamivudine as confirmed by XRPD. No other forms of lamivudine were detected.

TABLE 4

| LMV (g) | LMV Solution Temp (° C.) | Solvent System | Crystn Temp (° C.) | Water Activity | Form I Seed (g) | Yield (%) |
|---|---|---|---|---|---|---|
| 5.1 | 50 | 25 wt. % water-EtOH (29.5 mL) | 5 | 0.68 | 0.67 | 10% |

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entireties into the disclosure.

What is claimed is:

1. A thermodynamically controlled process for preparing Form I of lamivudine which comprises crystallizing Form I at a temperature T of from about 0° C. to about 50° C. from a mixture which comprises (a) lamivudine or an acid salt thereof or both, (b) a solvent system comprising water and at least one organic solvent, wherein the water activity of the solvent system is maintained in a range of from about $A_{w1}$ to about $A_{w2}$ during the crystallizing step, wherein $A_{w1}=(0.00458\times T)+0.506$ and $A_{w2}=(0.00316\times T)+0.775$, and optionally (c) Form I seed; wherein, when a lamivudine acid salt is employed in the mixture, the crystallizing step is conducted in the presence of a base; and wherein the water activity $A_w$ of the solvent system is maintained in a range in which Form I is thermodynamically the most stable form of lamivudine; and provided that when the solvent system is a binary solvent system and the temperature T is in a range of from about 20° C. to about 30° C. and the mixture from which Form I is crystallized is a slurry of Form I and Form II in the binary solvent system and the process does not employ an acid salt of lamivudine, then the organic solvent in the binary system is other than ethyl acetate.

2. The process according to claim 1, wherein the solvent system is a binary system of water and one organic solvent.

3. The process according to claim 2, wherein: (i) the mixture is a slurry of lamivudine acid salt and, when seeding is employed, the Form I seed in the solvent system, and (ii) the crystallizing step is conducted in the presence of base.

4. The process according to claim 3, wherein the base is incrementally added to the slurry during the crystallizing step.

5. The process according to claim 4, wherein the base is selected from the group consisting of alkali metal hydroxides, alkali metal carbonates, and tertiary amines, and is employed in an amount of at least one equivalent per equivalent of lamivudine acid salt.

6. The process according to claim 4, wherein the lamivudine acid salt is selected from the group consisting of organocarboxylates, organodicarboxylates, sulfate, bisulfate, nitrate, and hydrohalides.

7. The process according to claim 4, wherein the solvent system is a binary system and the organic solvent is selected from the group consisting of $C_{3-8}$ alkanones and $C_{1-8}$ alkyl acetates.

8. The process according to claim 7, wherein:
the base is selected from the group consisting of alkali metal hydroxides, alkali metal carbonates, and tertiary amines and is employed in an amount of at least one equivalent per equivalent of lamivudine acid salt; and
the lamivudine acid salt is selected from the group consisting of organocarboxylates, organodicarboxylates, sulfate, bisulfate, nitrate, and hydrohalides.

9. The process according to claim 8, wherein:
the organic solvent in the solvent system is 2-butanone, ethyl acetate or isopropyl acetate;
the base is triethylamine; and
the salt is lamivudine salicylate.

10. The process according to claim 9, wherein the crystallization is conducted using any one of the following solvent systems at the indicated temperature:

| Organic Solvent | Water Content (wt. %) | Temperature (° C.) | $A_W$ |
|---|---|---|---|
| IPAc | 1.1-1.7 | 25 | 0.62-0.85 |
| IPAc | 1.8-2.5 | 50 | 0.74-0.93 |
| IPAc | 1.1-1.7 | 20-30 | 0.59-0.85 |
| IPAc | 1.2-1.5 | 23-27 | 0.64-0.77 |
| EtOAc | 1.6-2.4 | 25 | 0.63-0.83 |
| EtOAc | 2.7-4.0 | 50 | 0.73-0.93 |
| EtOAc | 2.7-3.7 | 40-50 | 0.74-0.92 |
| 2-butanone | 3.5-6.0 | 25 | 0.62-0.84 |
| 2-butanone | 4.5-6.0 | 23-27 | 0.72-0.84. |

11. The process according to claim 2, wherein the mixture is an admixture of a first component containing lamivudine acid salt dissolved in a first amount of the solvent system and a second component containing a second amount of the solvent system, base and, when seeding is employed, the Form I seed.

12. The process according to claim 11, wherein the admixture is formed by adding the first component to the second component, wherein the first component has a temperature higher than T prior to the addition, and the admixture is maintained at temperature T during the crystallizing step.

13. The process according to claim 12, wherein the base is selected from the group consisting of alkali metal hydroxides, alkali metal carbonates, and tertiary amines, and is employed in an amount of at least one equivalent per equivalent of lamivudine acid salt.

14. The process according to claim 12, wherein the lamivudine acid salt is selected from the group consisting of organocarboxylates, organodicarboxylates, sulfate, bisulfate, nitrate, and hydrohalides.

15. The process according to claim 12, wherein the solvent system is a binary system and the organic solvent is selected from the group consisting of di-$C_{1-5}$ alkyl ethers, $C_{4-6}$ cyclic ethers, and $C_{3-5}$ dioxanes.

16. The process according to claim 15, wherein:
the base is selected from the group consisting of alkali metal hydroxides, alkali metal carbonates, and tertiary amines and is employed in an amount of at least one equivalent per equivalent of lamivudine acid salt; and
the lamivudine acid salt is selected from the group consisting of organocarboxylates, organodicarboxylates, sulfate, bisulfate, nitrate, and hydrohalides.

17. The process according to claim 16, wherein:
the organic solvent in the solvent system is THF;
the base is triethylamine; and
the salt is lamivudine salicylate.

18. The process according to claim 17, wherein the crystallization is conducted using either of the following THF-water systems at the indicated temperature:

| Organic Solvent | Water Content (wt. %) | Temperature (° C.) | $A_W$ |
|---|---|---|---|
| THF | 3-8 | 25 | 0.66-0.83 |
| THF | 1.5-6.0 | 0 | 0.52-0.80. |

19. The process according to claim 2, wherein the mixture is an admixture of (i) a solution of lamivudine dissolved in a first amount of the solvent system and (ii) a second amount of the solvent system containing, when seeding is employed, the Form I seed; and wherein the process does not employ an acid salt of lamivudine.

20. The process according to claim 19, wherein the admixture is formed by adding the solution of lamivudine to the second amount of the solvent system wherein:
(i) the second amount is at temperature T,
(ii) the lamivudine solution has a temperature higher than T, and
(iii) the admixture is maintained at temperature T during the crystallizing step.

21. The process according to of claim 20, wherein solvent system is a binary system and the organic solvent is selected from the group consisting of $C_{3-8}$ alkanones and $C_{1-8}$ alkyl alcohols.

22. The process according to claim 21, wherein the organic solvent is selected from the group consisting of 2-butanone, ethanol, and 1-propanol.

23. The process according to claim 22, wherein the crystallization is conducted using any one of the following solvent systems at the indicated temperature:

| Organic Solvent | Water Content (wt. %) | Temperature (° C.) | $A_W$ |
|---|---|---|---|
| 1-PrOH | 5.4-12.1 | 5 | 0.53-0.79 |
| EtOH | 13.9-43.0 | 5 | 0.53-0.79 |
| 2-butanone | 3.4-6.1 | 25 | 0.52-0.87. |

24. The process according claim 1, wherein Form I is substantially free of other forms of lamivudine.

25. The process according to claim 1, wherein Form I is substantially pure.

* * * * *